(12) United States Patent
He et al.

(10) Patent No.: US 11,457,987 B2
(45) Date of Patent: Oct. 4, 2022

(54) MANIPULATOR DEVICE AND THERAPEUTIC AND DIAGNOSTIC METHODS

(71) Applicant: The Johns Hopkins University, Baltimore, MD (US)

(72) Inventors: Xingchi He, Columbia, MD (US); Iulian I. Iordachita, Lutherville-Timonium, MD (US); Vincent Van Geirt, Sartrouville (FR); Peter Gehlbach, Baltimore, MD (US); Russell Taylor, Severna Park, MD (US)

(73) Assignee: The Johns Hopkins University, Baltimore, MD (US)

( * ) Notice: Subject to any disclaimer, the term of this patent is extended or adjusted under 35 U.S.C. 154(b) by 135 days.

(21) Appl. No.: 15/574,483

(22) PCT Filed: May 13, 2016

(86) PCT No.: PCT/US2016/032512
§ 371 (c)(1),
(2) Date: Nov. 15, 2017

(87) PCT Pub. No.: WO2016/187056
PCT Pub. Date: Nov. 24, 2016

(65) Prior Publication Data
US 2018/0125596 A1 May 10, 2018

Related U.S. Application Data

(60) Provisional application No. 62/162,550, filed on May 15, 2015.

(51) Int. Cl.
*A61B 34/30* (2016.01)
*A61B 17/29* (2006.01)
(Continued)

(52) U.S. Cl.
CPC .............. *A61B 34/77* (2016.02); *A61B 34/71* (2016.02); *A61B 34/72* (2016.02);
(Continued)

(58) Field of Classification Search
CPC .... A61B 2017/003; A61B 2017/00305; A61B 2017/00318; A61B 2017/00323;
(Continued)

(56) References Cited

U.S. PATENT DOCUMENTS 5,271,381 A * 12/1993 Ailinger ............... A61B 1/0055
　　　　　　　　　　　　　　　　　　138/120
5,397,323 A 　 3/1995 Taylor et al.
(Continued)

FOREIGN PATENT DOCUMENTS

WO 　 2014005583 A1 　 1/2014

OTHER PUBLICATIONS

Kim et al., "A sliffness-adjustable hyperredundant manipulator using a variable neutrallline mechanism for minimally invasive surgery", IEEE Trans Robotics, 30(2), pp. 382-395 (2014).
(Continued)

*Primary Examiner* — Katherine H Schwiker
(74) *Attorney, Agent, or Firm* — Fox Rothschild LLP (57) ABSTRACT

Dexterous manipulation devices are provided having an end effector enabling large curvature with a diameter of 1 mm or less that can articulate about an axis in a working space of about or less than 4 mm by 4 mm. Preferred devices are robotically actuated and controlled and can be used for a variety of therapeutic and diagnostic applications.

23 Claims, 9 Drawing Sheets

(51) Int. Cl.
| | |
|---|---|
| *A61B 34/00* | (2016.01) |
| *A61F 9/007* | (2006.01) |
| *A61B 17/00* | (2006.01) |
| *A61F 9/00* | (2006.01) |
| *A61M 25/00* | (2006.01) |
| *A61M 25/01* | (2006.01) |

(52) U.S. Cl.
CPC .......... *A61F 9/00727* (2013.01); *A61B 17/29* (2013.01); *A61B 34/30* (2016.02); *A61B 2017/00314* (2013.01); *A61B 2017/00327* (2013.01); *A61B 2034/306* (2016.02); *A61B 2034/715* (2016.02); *A61F 9/0008* (2013.01); *A61M 25/0084* (2013.01); *A61M 25/0147* (2013.01); *A61M 2210/0612* (2013.01)

(58) Field of Classification Search
CPC .. A61B 2017/00327; A61B 2017/2901; A61B 2017/2905; A61B 2017/2927; A61B 2017/2929; A61B 17/3417; A61B 17/34; A61B 34/77; A61B 1/0055; A61B 1/008; A61B 1/0056; A61B 1/0057; A61B 2017/2908; A61B 2034/306; A61B 34/30; A61M 25/0133; A61M 25/0138; A61M 25/0141; A61M 25/0147; A61M 25/0105; A61M 25/0144; A61F 9/007; A61F 9/00709; A61F 9/00; A61F 9/008; A61F 9/0017; A61F 9/0023; A61F 9/0061; A61F 9/00718; A61F 9/00727; A61F 9/00736; A61F 9/00754; A61F 9/00763; A61F 9/00772; A61F 9/00781

See application file for complete search history.

(56) References Cited

U.S. PATENT DOCUMENTS

| | | | | |
|---|---|---|---|---|
| 5,645,564 | A * | 7/1997 | Northrup | A61B 17/12022 606/205 |
| 5,772,597 | A * | 6/1998 | Goldberger | A61B 5/0084 600/473 |
| 6,270,453 | B1 * | 8/2001 | Sakai | A61B 1/0055 600/141 |
| 6,786,896 | B1 * | 9/2004 | Madhani | B25J 9/1615 606/1 |
| 7,217,263 | B2 | 5/2007 | Humayun et al. | |
| 7,850,642 | B2 | 12/2010 | Moll et al. | |
| 2005/0096694 | A1 | 5/2005 | Lee | |
| 2005/0107667 | A1 * | 5/2005 | Danitz | A61B 1/0053 600/139 |
| 2005/0222499 | A1 * | 10/2005 | Banik | A61B 1/00059 600/132 |
| 2006/0041188 | A1 * | 2/2006 | Dirusso | A61B 1/0055 600/146 |
| 2006/0199999 | A1 * | 9/2006 | Ikeda | A61B 1/00149 600/141 |
| 2008/0300462 | A1 * | 12/2008 | Intoccia | A61B 1/00071 600/146 |
| 2009/0171159 | A1 * | 7/2009 | Jorgensen | A61B 1/05 600/139 |
| 2010/0160735 | A1 * | 6/2010 | Bakos | A61B 17/3417 600/141 |
| 2010/0228284 | A1 | 9/2010 | Cooper et al. | |
| 2010/0331858 | A1 | 12/2010 | Simaan et al. | |
| 2011/0106145 | A1 * | 5/2011 | Jeong | A61B 17/29 606/205 |
| 2011/0125165 | A1 | 5/2011 | Simaan et al. | |
| 2011/0277580 | A1 | 11/2011 | Cooper et al. | |
| 2012/0041450 | A1 * | 2/2012 | Awtar | A61B 17/2909 606/130 |
| 2012/0197241 | A1 * | 8/2012 | Golden | A61B 1/0055 606/1 |
| 2012/0215220 | A1 * | 8/2012 | Manzo | A61B 18/1445 606/46 |
| 2012/0310254 | A1 * | 12/2012 | Manzo | A61B 34/71 606/130 |
| 2013/0144274 | A1 * | 6/2013 | Stefanchik | A61B 17/2909 606/1 |
| 2013/0255410 | A1 * | 10/2013 | Lee | F16H 19/08 74/89.22 |
| 2013/0304084 | A1 | 11/2013 | Beira et al. | |
| 2013/0312564 | A1 * | 11/2013 | Kim | B25J 18/06 74/490.04 |
| 2014/0163327 | A1 * | 6/2014 | Swanstrom | A61B 17/29 600/235 |
| 2014/0350337 | A1 | 11/2014 | Simaan et al. | |
| 2014/0350462 | A1 * | 11/2014 | Ataollahi | A61M 25/0147 604/95.04 |
| 2014/0379000 | A1 * | 12/2014 | Romo | A61B 34/71 606/130 |
| 2015/0047454 | A1 * | 2/2015 | Cooper | A61B 34/30 74/490.06 |
| 2016/0166343 | A1 | 6/2016 | Poon et al. | |
| 2016/0235274 | A1 * | 8/2016 | Graham | A61B 1/0011 |
| 2017/0095234 | A1 * | 4/2017 | Prisco | A61B 17/3478 |

OTHER PUBLICATIONS

Noonan et al., "A modular, mechatronic joint design for a flexible access platform for MIS", IEEE/RSJ International Conference on Intelligent Robots and Systems (Dec. 5, 2011).
Degani et al., "Percutaneous Intrapericardial Interventions Using a Highly Articulated Robotic Probe", IEEE/RAS-EMBS International Conference on Biomedical Robotics and Biomechatronics (2006).
Simaan et al., "Snake-like units using flexible backbones and actuation redundancy for enhanced minaturization", IEEE International Conference on Robotics and Automation (2005).
Ding et al., "Design, Simulation and Evaluation of Kinematic Alternatives for Insertable Robotic Effectors Platforms in Single Port Access Sugery", IEEE International Conference on Robotics and Automation (2010).
Kutzer et al., "Design of a new cable-driven manipulator with a large open lumen: Preliminary applications in the minimally-invasive removal of osteolysis", IEEE International Conference on Robotics and Automation (2011).
Qi et al., "A novel continuum-style robot with multilayer compliant modules", IEEE/RSJ International Conference on Intelligent Robots and System (2014).
Roppenecker et al., "Multi arm snake-like robot kinematics", IEEE/RSJ International Conference on Intelligent Robots and Systems (2013).
Swaney et al., "A flexure-based steerable needle: high curvature with reduced tiseue damage", IEEE Transactions on Biomedical Engineering, 60(4), pp. 906-909 (Apr. 2013).
Losey et al., "A flexure-based wrist for needle-sized surgical robots", SPIE Medical Imaging, Mar. 2013; 8671:86 711G-1.
Moses et al., "A continuum manipulator made of interlocking fibers", IEEE International Conference on Robotics and Automation (2013).
Jelinek et al., "Classification of joints used in steerable instruments for minimally invasive surgery—a review of the state of the art", J. Med. Devices, 9(1), 010801, Mar. 1, 2015.
Moorthy et al., "Dexterity enhancement with robotic surgery", Surg. Endosc., 18(5), pp. 790-795 (May 2004).
Dogramaci et al., "Dynamics of epiretinal membrane removal off the retinal surface: a computer simulation project", Br. J. Ophthalmol, 97(9), pp. 1202-1207 (Sep. 2013).
Kadanosono et al., "An experimental study of retinal endovascular surgery with a microfabricated needle", Invest. Ophthalmol Vis. Sci., 52(8), pp. 5790-5793 (Jul. 29, 2011).
Ergeneman et al., "Characterization of Puncture Forces for Retinal Vein Cannulation", J. Med. Devices, 5(4), 044504, Nov. 15, 2011.
Taylor et al., "A Steady-Hand Robotic System for Microsurgical Augmentation", Int. J. Rob. Res., 18(12), pp. 1201-1210 (Dec. 1999).

(56) References Cited

OTHER PUBLICATIONS

Mitchell et al., "Development and Application of a New Steady-Hand Manipulator for Retinal Surgery", IEEE International Conference on Robotics and Automation (2007).

Uneri et al., "New Steady-Hand Eye Robot with Micro-force Sensing for Vitreoretinal Surgery", IEEE International Conference on Biomedical Robotics and Biomechatronics (2010).

He et al., "Toward Clinically Applicable Steady-Hand Eye Robot for Vitreoretinal Surgery", ASME 2012 International Mechanical Engineering Congress and Exposition, vol. 2, Biomedical and Biotechnology.

Gijbels et al., "Design and Realisation of a Novel Robotic Manipulator for Retinal Surgery", IEEE/RSJ International Conference on Intelligent Robots and Systems (2013).

Charles et al., "Dexterity-enhanced telerobotic microsurgery", IEEE International Conference on Advanced Robotics (1997).

Nakano et al., "A parallel robot to assist vitreoretinal surgery", Int. J. Comput. Assist. Radiol. Surg., 4(6), pp. 517-526 (Nov. 4, 2009).

Meenink et al., "Vitreo-retinal eye surgery robot: sustainable precision" Ph.D. Dissertation, Technische Universiteit Eindhoven (2011).

Ida et al., "Microsurgical robotic system for vitreoretinal surgery", Int. J. Comput. Assist. Rediol. Surg., 7(1), pp. 27-34 (Jan. 7, 2012).

Wei et al., "Design and theoretical evaluation of micro-surgical manipulators for orbital manipulation and intraocular dexterity", IEEE International Conference on Robotics and Automation (2007).

Yu et al., "Design, calibration and preliminary testing of a robotic telemanipulator for OCT guided retinal surgery", International Conference on Robotics and Automation (2013).

Nasseri et al., "The introduction of a new robot for assistance in ophthalmic surgery", Conf. Proc. IEEE Eng. Med. Biol. Soc. 2013, 5682-5685 (2013).

Gijbels et al., "Design of a teleoperated robotic system for retinal surgery", IEEE International Conference on Robotics and Automation (2014).

MacLachlan et al., "Micron: An Actively Stablized Handheld Tool for Microsurgery", IEEE Transactions on Robotics, 28(1), pp. 195-212 (2012).

Song et al., "Fiberoptic OCT sensor guided "SMART" microforceps for microsurgery", Biomed. Opt. Express, 4(7), pp. 1045-1050 (Jul. 1, 2013).

Kummer et al., "OctoMag: An Electromagnetic System for 5-DOF Wireless Micromanipulation", IEEE Transactions on Robotics, 26(6), pp. 1006-1017 (2010).

Wei et al., "Performance evaluation for multi-arm manipulation of hollow suspended organs", IEEE Transactions on Robotics, 25(1), pp. 147-157 (2009).

Wei et al., "Modeling, force sensing, and control of flexible cannulas for microstent delivery", J. Dyn. Sys., Meas., Control, 134(4), 041004 (Apr. 2012).

Gonenc et al., "Force-Sensing Microneedle for Assisted Retinal Vein Cannulation", Proc. IEEE Sens. 2014, pp. 698-701 (Nov. 2014).

Cheng et al., "Design and Analysis of a Robust, Low-cost, Highly Articulated Manipulator Enabled by Jamming of Granular Media", IEEE International Conference on Robotics and Automation (2012).

Jiang et al., "Design of a variable stiffness flexible manipulator with composite granular jamming and membrane coupling", IEEE/RSJ International Conference on Intelligent Robots and Systems (2012).

Cianchetti et al., "STIFF-FLOP surgical manipulator: mechanical design and experimental characterization of the single module", IEEE/RSJ International Conference on Intelligent Robots and Systems (2013).

\* cited by examiner

SECTION A-A

SECTION B-B

MANIPULATOR DEVICE AND THERAPEUTIC AND DIAGNOSTIC METHODS

RELATED APPLICATIONS

This application is the U.S. national stage pursuant to 35 U.S.C. § 371, of United States International Application Ser. No. PCT/US2016/032512, filed May 13, 2016 and published in English on Nov. 24, 2016 as publication WO 2016/187056 A1, which claims the benefit of priority under 35 U.S.C. § 119(e) to U.S. Provisional Application No. 62/162,550, filed May 15, 2015, which are incorporated herein by reference in their entirety.

FIELD

The present disclosure relates generally to manipulator devices, and in preferred aspects, to high dexterity sub-millimetric robotic devices.

BACKGROUND

Figure 1:
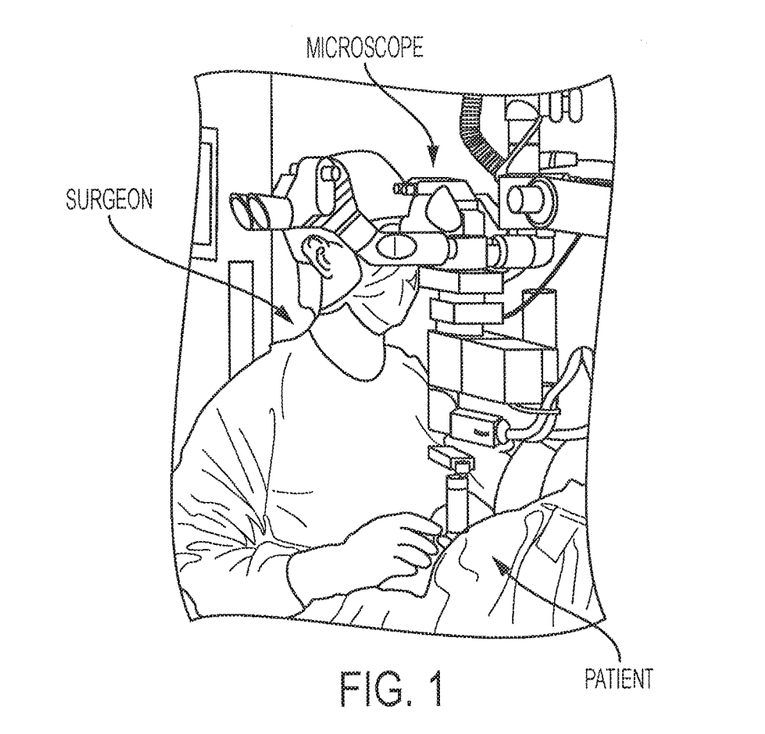
FIG. 1 a perspective view of a surgeon and a patient in a clinical environment.

Retinal microsurgery refers to a family of microsurgical procedures that treat retinal diseases such as retinal detachment macular hole, diabetic retinopathy, epiretinal membrane, and with emerging application to retinal vein occlusion and others. Retinal microsurgery is one of the most technically challenging and high consequence surgical disciplines. In the operating room, a surgical microscope is positioned above the patient's eye to provide magnified visualization of the posterior of the eye, as shown in FIG. 1. Small instruments, e.g., 23 Ga with 0.65 mm diameter, are inserted through trocars on the sclera to operate at the back of the eye. The surgeon needs to control the instrument motion in a very fine and precise manner to handle the delicate eye tissue. Due to the trocar constraint at the sclerotomy, the instrument motion is coupled with the eye movement. If the surgeon intends to keep the patient's eye still, only three rotational degrees of freedom (DOF) about the sclerotomy and one translational DOF along the instrument axis are allowed. This concept is termed as remote center-of-motion (RCM) in robotics. The lateral translation of the tool will move the patient's eye, causing change of the view in the microscope and possibly relative motion between the instrument and the retina, which is potentially risky when the instrument tip is close to the retina. This constraint limits not only the instrument workspace inside the patient's eye, but also the orientation of the instrument at a given position. A similar problem exists in laparoscopic surgery.

Figure 2:
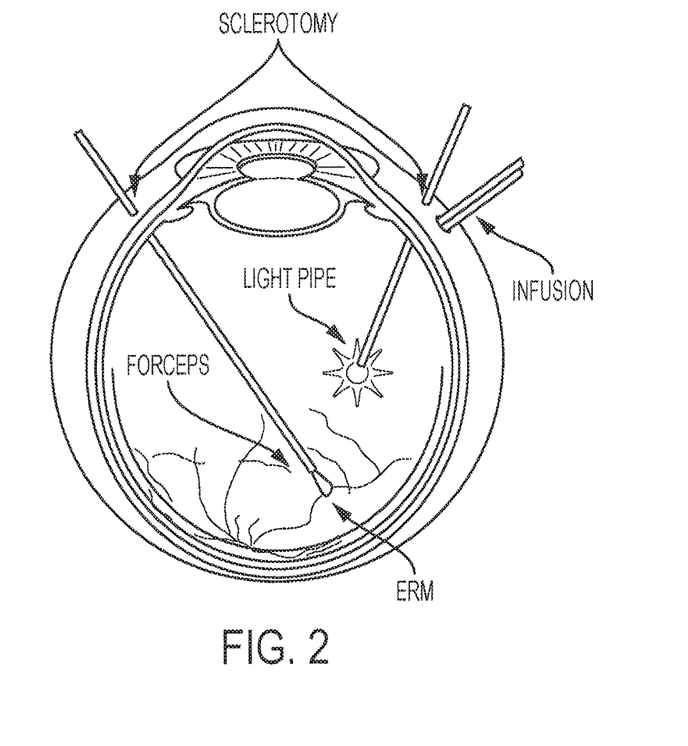
FIG. 2 is an exemplary cross sectional perspective view of the layout of surgical instruments within an eye.

In retinal microsurgery, instrument dexterity at the distal end can potentially be very useful. A prototypical retinal procedure is epiretinal membrane (ERM) peeling. ERM is a thin, semitransparent layer of scar tissue that forms on the surface of the retina. It induces surface stress on the retina that results in wrinkles and striae that distort both the retinal surface and the patient's vision. In ERM peeling, the surgeon typically uses a micro-forceps tool to carefully grasp the edge of the membrane, and slowly delaminate it off of the retinal surface, as shown in FIG. 1. Besides straight instruments, angled instruments are available to enable approaching the membrane with different tool orientations, e.g., 45 degree delamination spatula and pic, as well as vertical 90 degree scissors. Incorporating additional DOFs at the distal end of the instrument, can provide more flexibility for the surgeon to grasp the membrane at the optimum angle, and to control the peeling trajectory thereby minimizing shear stress on the retina. Another extremely difficult procedure is retinal vein cannulation (RVC) that has the potential to treats retinal vein occlusion. In this procedure a therapeutic agent, e.g., plasminogen activator (t-PA), is directly injected into the occluded vein using a micropipette. Retinal veins are typically less than 100 µm in diameter. The micropipette needs to puncture the retinal vein, and to stay within the vessel for drug delivery. FIG. 2 illustrates a simulated RVC, in which a 70 µm micropipette is used to inject air into the vessel of a chorioallantoic membrane. Using an angled micropipette, e.g., 30 degrees or aiming a straight micropipette at the vessel with an advantageous angle, e.g., 4 degrees that can allows a more gradual approach to the retina vein, and potentially improve safety by reducing the likelihood of puncturing through the retina vein. Surgical instruments such as these, with angled tips provide a suboptimal solution that requires multiple instruments, cumbersome surgical workflow, and less than optimum success rates and safety.

Certain robotic systems for retinal microsurgery have been developed to enhance natural human capabilities. The main approaches are hands-on cooperatively controlled systems, master-slave teleoperated systems, handheld robotic devices, and untethered micro-robots. The untethered micro-robots have the least constraints on workspace and manipulability, can overcome many current limitations if they can deliver sufficient force and the surgical workflow can be adapted accordingly. A pre-curved concentric nitinol tubes approach has been investigated to provide intraocular dexterity. Microstent delivery into the retinal vessel was attempted. The maximum curvature to pre-bend a nitinol tube poses the challenge on balancing the length of the dexterous wrist mechanism and the range of motion, i.e., maximum rotation angle.

SUMMARY

Herein we provide new manipulation devices that can provide high dexterity within a small workspace.

In one aspect, preferred devices include a dexterous end-effector having a diameter or cross-section of 1 mm or less and that can articulate about an axis in a small working space such as less than 4 mm by 4 mm or 3 mm by 3 mm. Preferred devices also provide large curvature and have a large range of motion such as up to and greater than 45, 60, 90 or 120 degrees around one or more axes of rotation.

Thus, in another aspect, preferred devices include a manipulation device comprising a dexterous end-effector having a diameter of 1 mm or less, that provide greater than 45-degrees, or 60-degrees or 90-degrees of rotation and can articulate about an axis in a small working space such as less than 4 mm by 4 mm or 3 mm by 3 mm.

In a further aspect, preferred devices include a snake-like manipulation device comprising having a diameter of 1 mm or less, that provide greater than 45-degrees, or 60-degrees or 90-degrees of rotation and can articulate about an axis in a small working space such as less than 4 mm by 4 mm or 3 mm by 3 mm. The present snake-like devices comprise multiple conjoined units that include the end effector unit.

In a yet further aspect, preferred devices include a multi-segment manipulation device comprising a dexterous end-effector having a diameter of less than 1 mm and that provide greater than 45-degrees, or 60-degrees or 90-degrees of rotation and can articulate about an axis in a small working space such as less than 4 mm by 4 mm or 3 mm by 3 mm.

Preferred devices can be employed for a variety of clinical applications including where a surgical tool is used in the range of 19 Gauge (about 1 mm diameter or cross-section) to as small as about 25-26 Gauge (about 0.4 to 0.5 mm in diameter of cross-section).

Thus, in a preferred aspect, a dexterous manipulation device is provided that comprises an end effector that 1) has a cross-section of from 0.4 mm to 1 mm; 2) can articulate in a working space less than 4 mm by 4 mm; and 3) has greater than 90-degrees of rotation with two degrees of freedom.

In another preferred aspect, a snake-line dexterous manipulation device is provided that comprises an end effector that 1) has a cross-section of from 0.4 mm to 1 mm; 2) can articulate in a working space less than 4 mm by 4 mm; and 3) has greater than 90-degrees of rotation with two degrees of freedom In some embodiments, the end effector suitably may be 1 mm or less in diameter or cross-section, and preferably may be less than 0.9 mm or 0.8 mm in diameter or cross-section. In certain embodiments, the end effector length may be less than 0.6 or 0.5 mm in diameter or cross-section. Preferred end effectors include those having a diameter or cross-section of from about 0.4, 0.5 or 0.6 mm to 1 mm, including end effectors having a diameter or cross-section of about 0.5, 0.6, 0.7, 0.8, 0.9 or 1 mm in diameter or cross-section.

Devices of the invention may be manually operated or more preferably robotically actuated and controlled.

Devices of the invention can be used to access and treat a variety of patient sites and tissue, including within a patient's eye, sinus, ear and other sites, including sites that have small dimensions. Devices of the invention are particularly useful for a variety of Ear, Nose Throat (ENT) surgical procedures. Devices of the invention also will be useful to guide a needle to or within tissue of a patient for a percutaneous procedure. Thus, a device of the invention could include a snake-like wrist close to a needle tip that would bend in two directions according to the desired needle tip trajectory.

Preferred devices can provide tissue access at a desired procedural angle in an otherwise constrained space. Devices of the invention can be used for example to observe, sample, deliver secondary technology or to directly manipulate targeted patient tissue. Devices of the invention provide an access platform for desired tool function, for example, fiber optics, laser probes, illumination probes, biopsy mechanism, cannulas, any of a variety of surgical tools as well as for delivery of any of a variety of therapeutic or diagnostic agents such as imaging agents, small molecule drugs, peptide or nucleic acid based therapeutic agents, and stem cells, among others.

In some embodiments, the device may further include an actuation unit as well as a body unit that mates with the end effector and actuation unit.

In some embodiments, the actuation unit may include a housing, a motion scaling system, a motor and a plurality of pulleys with an actuation system. In some embodiments, the body unit may include an actuation system having a plurality of actuation wires extending from a distal end to a proximal end of the body unit through an inner lumen of the body unit.

In other embodiments, an end effector may include a plurality of elements having curved cylindrical surfaces wherein, an axis of a top surface is orthogonal to a bottom surface thereby forming a rolling joint by assembling the elements in alternating orthogonal directions. A plurality of actuation wires can be coupled to a plurality of apertures disposed in the elements thereby aligning the elements.

In some embodiments, a motor of the actuation unit may be a linear motor. In other embodiments, a plurality of motors may initiate independent actuation of each actuation wire, thereby controlling the movement of the device. In some embodiments, the actuation wires have pretension arrangement.

The end effector of the device may comprise one or more of a variety of manipulation tools or devices. The device can thus function as a forceps, light pipe, laser probe, needle, pick, and endoscope, among others. In some embodiments, the end effector may include a forceps and the forceps may be suitably actuated by the actuation wires thereby controlling the movement. In other embodiments, the end effector may have a needle tip, including a steerable needle tip. In some embodiments, the end effector also may include a pipette. The end effector also may comprise an illumination unit.

In another aspect of the invention, a surgical system may include an actuation unit having a housing, an elongated cylindrical body having a hollow inner lumen; and an end effector having a diameter of less than 1 mm and a length of less than 3 for articulation in a working space less than 3 mm by 3 mm. In some embodiments, the surgical system may be an ophthalmological surgical system.

In some embodiments, a surgical system is provided that comprises a device as disclosed herein and preferably may include an actuation unit having a housing comprising a plurality of motors disposed within the housing, a motor scaling transmission disposed within the housing used for individual control of a lever mechanism, and a plurality of pulley guides to route a cabling system within the housing. In some embodiments, the surgical system may further include an elongated cylindrical body having a hollow inner lumen and a cabling system having a plurality of actuation wires extending from a proximal end to a distal end of the elongate cylindrical body thereby connecting the motor scaling transmission disposed in the housing through the elongate cylinder body. In other embodiments, the surgical system may include the end effector comprising a plurality of curved cylindrical disc elements having a top surface and a bottom surface with a plurality of apertures disposed within the disc element and the cabling system connect the disc elements through the apertures providing rotation about an axis and two degrees of rotational freedom.

In some embodiments, the system may include the top and bottom surfaces of adjacent disc elements to form a rolling joint. In other embodiments, the inner lumen may be configured to receive a pipette element. In other embodiments, the cabling system may provide redundant actuation wherein each actuation wire has an individual motor control mechanism.

In a further aspect, methods for treating a subject are provided comprising contacting tissue of the subject with a device as disclosed herein. In such methods the device may be for example inserted within an eye of the subject; the device may contact a sinus region of the subject; the device may be inserted within an ear of the patient; or the device may contact cardiac tissue of a subject, among others.

In another aspect of the invention, a method is provided for manipulating a robotic device as disclosed herein within a working space of less than 4 mm by 4 mm or 3 mm by 3 mm during a surgical procedure and inserting device as disclosed herein through or proximate to patient tissue; and manipulating the device which may include rotating a distal end of the device about two degrees of freedom and actuating the device to engage a bending angle.

In some embodiments, the device may be an intraocular device inserted within a patient eye during an ocular surgical procedure. In other embodiments, the surgical procedure may be a sinus surgery procedure. In some embodiments, the surgical procedure is a cochlear implant surgery. In some embodiments, the surgical procedure may be an intra-cardiac procedure. In some embodiments, the surgical procedure may be a subglottic or vocal cord procedure.

In another aspect of the invention, a device may include an actuation unit that includes a proximal portion and a distal portion, a cylindrical body that may include a proximal end and a distal end; and an end effector having a proximal end and a distal end. The proximal end of the cylindrical body may be configured to connect to the distal portion of the actuation unit. The distal end of the cylindrical body may be configured to be coupled to the proximal end of the end effector. The end effector may be configured to articulate about an axis in a working space less than 3 mm by 3 mm.

In some exemplary embodiments, the size of the end effector may be less than 0.9 mm in diameter. In some exemplary embodiments, the size of the end effector is less than 3 mm in length. Additionally, the robotic device may be an intra-ocular robotic device.

The actuation unit may further include the proximal portion having a housing, a motion scaling system, and a motor disposed therein and the distal portion having a plurality of pulleys and an actuation system may be disposed therein. The cylindrical body may further include an actuation system having a plurality of actuation wires that extend from the distal end to the proximal end of the cylindrical body through an inner lumen. An end effector may further include a plurality of elements having curved cylindrical surfaces. An axis of a top surface may be orthogonal to a bottom surface and may be configured to form a rolling joint by assembling the elements in alternating orthogonal directions. A plurality of actuation wires may be coupled to a plurality of apertures disposed in the elements and may be configured to align the elements.

In some embodiments, the device may include a linear motor. A plurality of motors may be configured to initiate independent actuation of each actuation wire. The plurality of actuation wires may have pretension arrangement. The motor may include a scaling transmission and may include a lever mechanism.

In other exemplary embodiments, the end effector may include a micro-forceps and the actuation wires may be configured to actuate the forceps. A proximal end of a cabling system may be configured to a pulley guide thereby configured to the motion scaling system. The cabling system may have a pre-tension value that may be configured to be adjusted via a pre-tension adjustment screw coupled to the motion scaling transmission.

Additionally, the end effector may include a steerable needle tip. A micro-forceps may be coupled to the distal end of the end effector. A micro-pipit may be coupled to the distal end of the end effector. A needle tip may be coupled to the distal end of the end effector.

In another aspect of the invention, a surgical system may include an actuation unit that includes a proximal portion and a distal portion having a housing. An elongated cylindrical body may include a hollow inner lumen that extends from a proximal end and a distal end of the elongated cylindrical body. An end effector may have a proximal end and a distal end wherein the distal end has a diameter of less than 1 mm and a length of less than 3 and may be configured to articulation in a working space less than 3 mm by 3 mm. The proximal end of the cylindrical body may be configured to connect to the distal portion of the actuation unit and the distal end of the cylindrical body may be configured to be coupled to the proximal end of the end effector.

In some embodiments, the actuation unit having a housing may include a plurality of motors disposed within the housing, a motor scaling transmission disposed within the housing configured to individually control a lever mechanism; and a plurality of pulley guides configured to route a cabling system within the housing. The elongated cylindrical body may include a cabling system having a plurality of actuation wires extending from a proximal end to a distal end of the elongate cylindrical body configured to connect the motor scaling transmission disposed in the housing through the elongate cylinder.

In other embodiments, the end effector may include a plurality of curved cylindrical disc elements having a top surface and a bottom surface with a plurality of apertures disposed within the disc element. The cabling system may connect the disc elements through the apertures configured to rotate about an axis and two degrees of rotational freedom. The top and bottom surfaces of adjacent disc elements may form a rolling joint. The inner lumen may be configured to receive a micro-pipet. The cabling system may provide redundant actuation wherein each actuation wire has an individual motor control mechanism. The surgical system may be an ophthalmological surgical system.

Other aspects of the invention are disclosed infra.

BRIEF DESCRIPTION OF THE DRAWINGS

Aspects of the present disclosure may be better understood with reference to the following drawings. Components of the drawing are not necessarily to scale, emphasis instead being placed upon clearly illustrating the principles of the present disclosure. Moreover, the drawings, like reference numerals designate corresponding parts throughout the several views.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," of "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the surgeon and the term "distal" refers to the portion located furthest from the surgeon. It will be further appreciated that for conciseness and clarity, spatial terms such as "vertical," "horizontal," "up," and "down" may be used herein with respect to the illustrated embodiments. However, surgical training instruments may be used in many orientations and positions, and these terms are not intended to be limiting and absolute.

In a preferred aspect, devices and methods are provided for ocular surgeries that allow a user to manipulate a sub-millimeter intra ocular robotic device. As a result of improving dexterity, the accuracy and efficiency of diagnostic or therapeutic capabilities in ophthalmology may be enhanced, thereby providing tissue access from an optimal surgical angle.

As discussed, devices and methods disclosed herein can be used with a variety of surgical devices, including measuring devices, sensing devices, locator devices and insertion devices, etc. Additionally, the device can be used in a variety of procedures, such as sinus surgery, cochlear implant surgery, subglottic and vocal cord procedures and intra-cardiac procedures.

The exemplary embodiments described herein generally relate to a robotic device for performing intraocular surgery. In some preferred embodiments, the device can include any one or more of the following elements: an actuation unit having a housing, a motion scaling system, a motor a plurality of pulleys and an actuation; a cylindrical body having an inner lumen; and an end effector having a plurality of curved cylindrical elements, forming a rolling joint by assembling the cylindrical elements in alternating orthogonal directions and a plurality of actuation wires. Components of the device preferably utilize a variable neutral-line mechanism to articulate and rotate an end effector having two degrees of freedom.

FIGS. 1-2 illustrate prior art embodiments of surgical techniques used in retinal microsurgery. FIG. 1 illustrates the position of a surgeon and a patient in a clinical setting. FIG. 2 illustrates a cross sectional view of surgical instruments disposed in the eye during a procedure.

Figure 3:
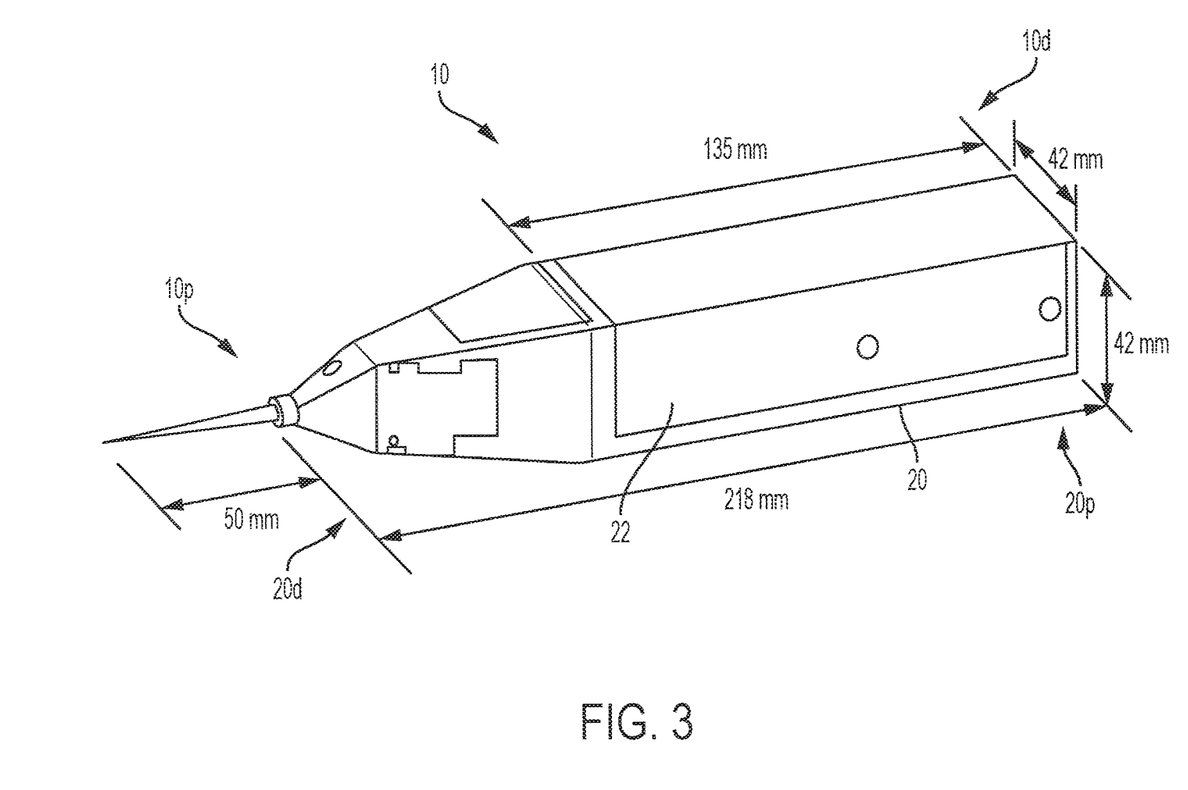
FIG. 3 is side perspective view of an exemplary embodiment of an ophthalmological surgical device.
Figures 5A, 5B:
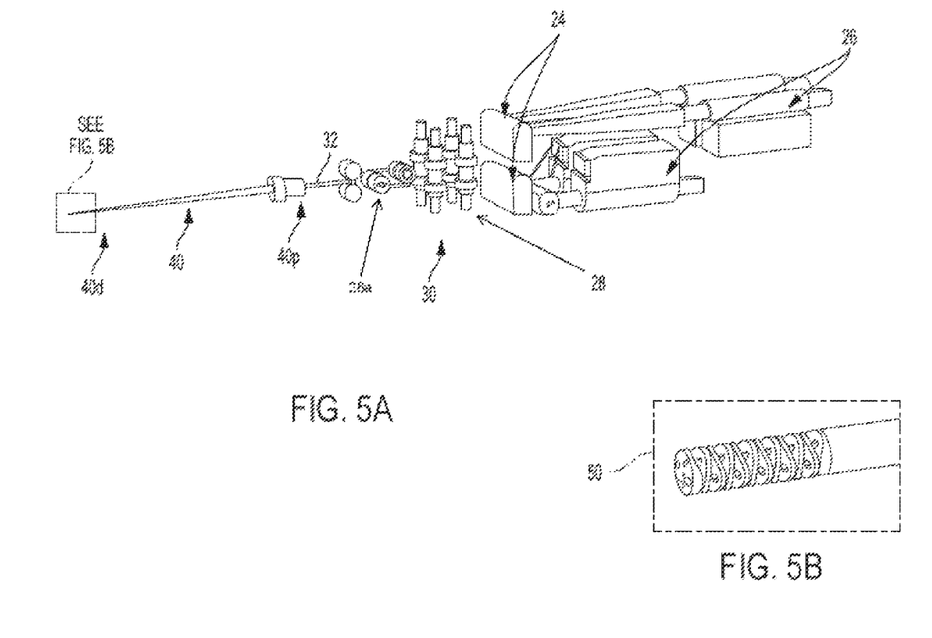
FIG. 5 is a is an exploded view of an exemplary embodiment of the ophthalmological surgical device as shown in FIG. 3.

As shown in FIGS. 3 and 5, one exemplary embodiment of a device 10 for preforming an intraocular surgery may include four motors, motion scaling transmissions, a set of pulley guides to route the wires, and the housing. FIG. 3 illustrates the design of the actuation unit and its housing. In some embodiments, the device 10 can have a proximal end 10p positioned proximate surgeon and a distal end 10d positioned within the ocular cavity. In an alternate embodiment, the device can be formed a plurality of control mechanism. For example, when the device is configured for redundant actuation a single or individual motor is used to control each individual actuation wire of the cabling system. As further discussed below, the device can increase the bending and rotation angles of a device.

Figure 6:
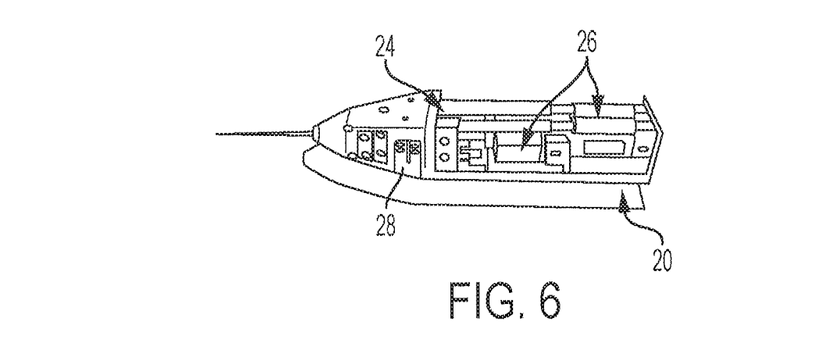
FIG. 6 is a side perspective with of an exemplary embodiment of the ophthalmological surgical device as shown in FIG. 3 without the housing.

As shown in FIGS. 3 and 6, an exemplary embodiment of the device may include an actuation unit 20 having an exterior housing 22 having an external surface exposed to the environment and an internal cavity configured to contain a motion scaling system 24, a motor 26, a plurality of pulleys 28, and an actuation system 30; a cylindrical body having an inner lumen. The distal end 20d of the actuation unit may be coupled to a proximal end 40p of the cylindrical body 40 having an inner lumen 42. Within the inner lumen 42 the actuation system 30 can extend from the housing 20 through the distal end of the housing 20d and from the proximal end 40p through the inner lumen 40 to the distal end 40d of the cylindrical body 40. The device 10 may further include an end effector 50. The actuation system 30 may extend from the distal end 40d of the cylindrical body to the end effector 50 thereby controlling the articulation and rotation of the end effector 50.

In other words, while the device has two DOFs, redundant actuation is suitably implemented for flexibility in control within a working space of less than 3 mm by 3 mm. In some embodiments four linear motors (e.g., L12, Firgelli Technologies, NC, Canada) are used to provide independent actuation of four wires. The travel lengths of the actuation wires for the same bending DOF are not necessarily symmetric, i.e., when one wire is retracted to pull the device to bend, the opposite wire needs to release a longer travel to balance the geometric constraint. In one exemplary system, the motors provide a stroke of 20 mm with a position resolution of 0.1 mm. In order to improve accuracy, a motion scaling transmission can he used for each wire. In some embodiments, the motion scaling is implemented with a lever mechanism. In certain preferred systems, the ratio between the moment arm for motor input and that for wire output can be 5:1. In certain preferred systems, the linear motion of the motor is translated to the lever rotation through a crank mechanism. In certain preferred systems, the motion scaling ratio between the linear motion of the motor and that of the wire is not fixed at 5:1, e.g., when the motor travel reaches 5 mm, the motion scaling ratio can drop to about 4.8:1. This relationship can be solved using geometric conditions. The actuation unit may be mounted on the distal end of cylindrical body for example fabricated from stainless steel. In a preferred system, a plurality of wires exit the proximal end of the cylindrical body, then slide around a set of pulley guides 28a to connect to the motion scaling transmissions. The wire pretensions can he adjusted, e.g. using screws on the levers. In some embodiments, the device can he used manually, particularly as a handheld tool. In other embodiments, the device can he mounted on a robotic instrument such as a Steady-Hand Eye Robot.

FIG. 5 is an exemplary exploded view of the internal components within the housing of the actuation unit of a preferred system. As shown in FIG. 5 a lever may be used to create a motion scaling system 24. In some embodiments the motor 26 can be linear, in other embodiments to compensate for a non-linear motor or a not fully linear motor a crank may be introduced. The neutral position of the lever is a vertical orientation and it has a zero angle and a symmetric range of motion. The proximal end of the cable 32 can be connected in the motion scaling system 24 thereby setting the pretension. A screw 34 may be used to modify the tension in the cable thereby altering the tightness of the screw the tension may be adjusted. The cable 32 may pass through the lever and a node will be tight in the proximal end of the cable. The housing 22 as shown in FIG. 3 has a minimal section size due to the actuators. Within the cavity of the housing a scaling ration of 5 may be integrated, which will result in having the same displacement as a larger scale structure.

Figure 4A:
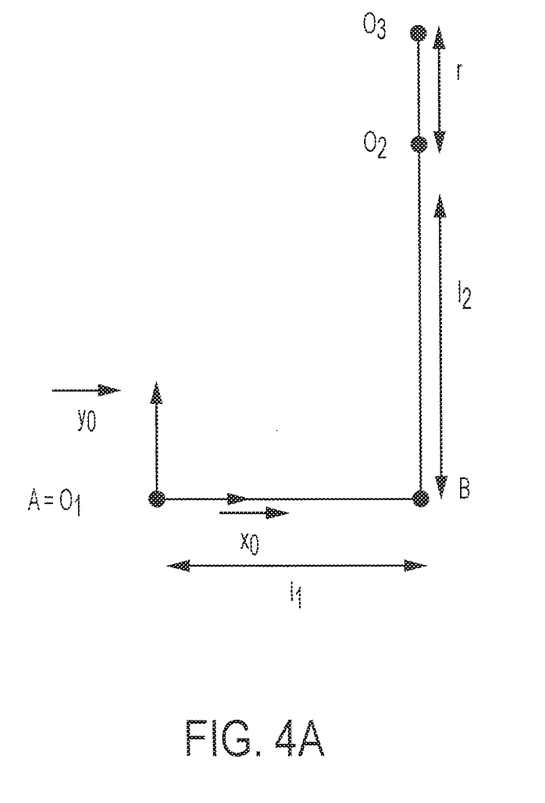
FIGS. 4A-4B are graphical representations illustrating the 4-bar mechanism scheme.
Figure 4B:
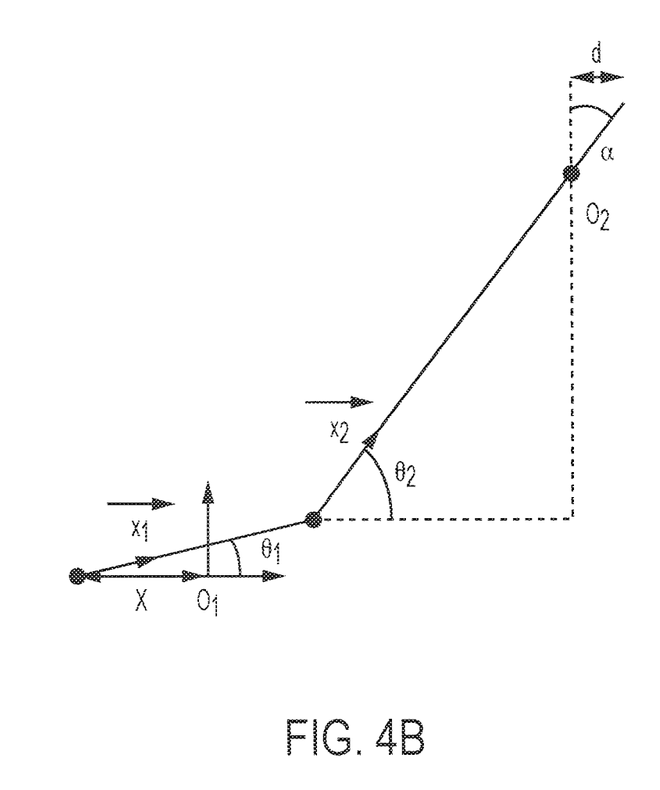

As shown in FIGS. 4A-4B, a 4-bar mechanism may be implemented. The points O1 and O2 are fixed to the housing. The x variable denote the input linear displacement of the motor. FIG. 4A illustrates a zero position and FIG. 4B illustrates an angled position of the 4-bar mechanism scheme.

The system may have the following vector chain.

$$\overrightarrow{O_1O_2} = \overrightarrow{O_1A} + \overrightarrow{AB} + \overrightarrow{BO_2}$$

with $$\overrightarrow{O_1A} = -x\overrightarrow{x_0}$$

$$\overrightarrow{AB} = l_1\overrightarrow{x_1}$$

$$\overrightarrow{BO_2} = l_2\overrightarrow{x_2}$$

$$\overrightarrow{O_1O_2} = l_1\overrightarrow{x_0} + l_2\overrightarrow{y_0}$$

One can project on $O_0$ frame:

$$\begin{cases} l_1 = l_1\overrightarrow{x_1}\cdot\overrightarrow{x_0} + l_2\overrightarrow{x_2}\cdot\overrightarrow{x_0} - x \\ l_2 = l_1\overrightarrow{x_1}\cdot\overrightarrow{y_0} + l_2\overrightarrow{x_2}\cdot\overrightarrow{y_0} \end{cases}$$

Which results in:

$$\begin{cases} l_1 = l_1\cos(\theta_1) + l_2\cos(\theta_2) - x \\ l_2 = l_1\sin(\theta_1) + l_2\sin(\theta_2) \end{cases}$$

Considering x as the input, a system can be obtained of 2 equations with 2 parameters to be determined. It has been numerically solved and the following curve represents the evolution of the ratio with an input range of [0 4.5]. The ratio is obviously calculated with x d.

The ratio is mostly given by the position of the center of rotation in the bar. Preferably, a ratio of 5 between the length 12 and r is utilized. The length of 11 is given by the motor distance to the motion scaling system. The evolution of this ratio can be integrated directly into the control, using a look-up table with the pre-computed values. Missing values can be linearly interpolated.

As further shown in FIG. 5 cables 32 coming from the distal flexure may be routed to be connected to the motion scaling system 24. This is made with a set of pulleys 28. In order to know the exact path of the cables, two pulleys 28 are needed to change the cable position. Typically, it may be necessary to change it in two planes; a set of 4 pulleys may be per cable may be preferred. For example, to minimize the friction, the pulleys may be mounted on bearings. The first set of pulleys separate the cables in two part: up and down, the second set split the cables left and right. In some embodiments, the two sets may be exchanged.

With this structure, a fine control is possible only by having a force-sensing loop, in order to control the forces in the cables and to avoid plastic deformation or destruction of the distal parts. According to the housing design, a preferred method to integrate them may be between the pulleys to route the cables and the motion scaling system. In some embodiments a force sensor may be included in the structure. Since the motion of the flexure is provided by the cable motion, the motors may be controlled in position. The control implemented may use the mathematical model to define the wire displacement with a given input bending angle. This displacement may be scaled according to the motion scaling system and then the motors may be controlled in position with the calculated value. It is an open-loop system.

In an alternate embodiment, the behavior can be approximated as linear only with small bending angles (up to 30°). A non-linear model may be preferred for larger angles.

Figure 7:
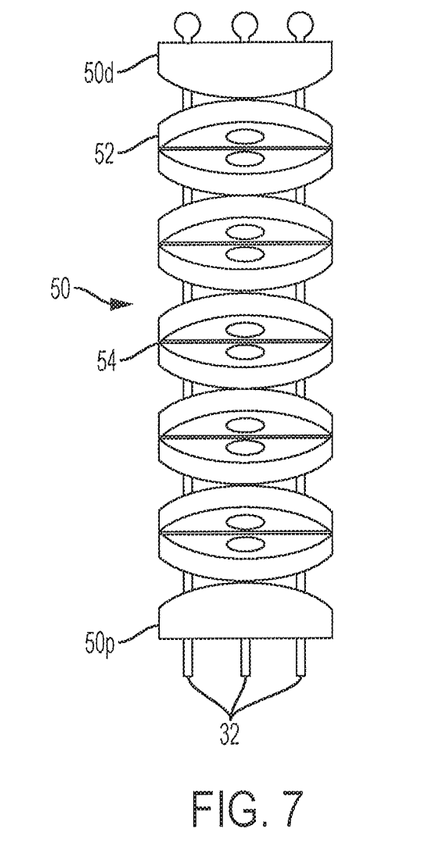
FIG. 7 is a detailed side perspective view of an exemplary embodiment of an end effector of the ophthalmological device as shown in FIG. 3.
Figure 8:
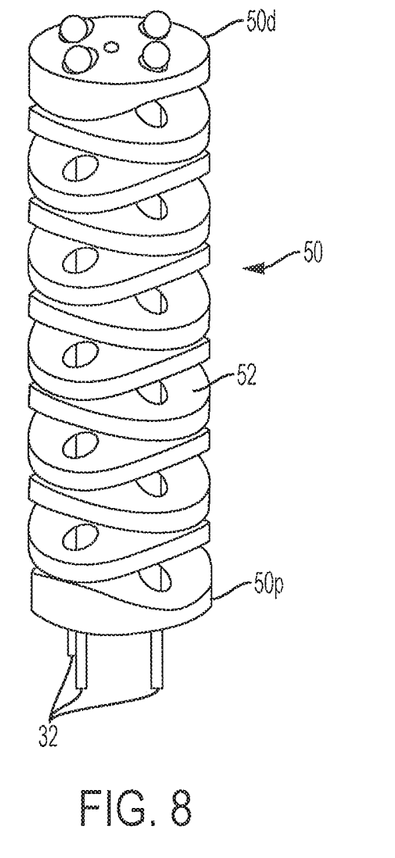
FIG. 8 is a front perspective view of an exemplary embodiment of the surgical device as shown in FIG. 3.
Figure 9:
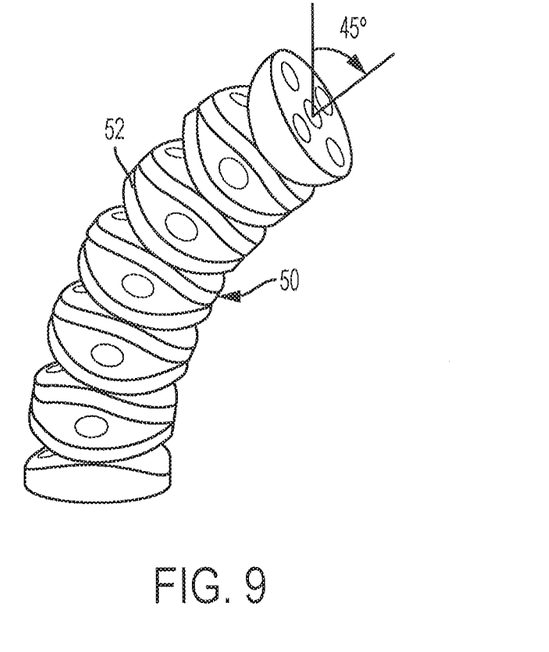
FIG. 9 is a front perspective view of an exemplary embodiment of the surgical device as shown in FIG. 3 articulated about a 45 degree angle.
Figure 10:
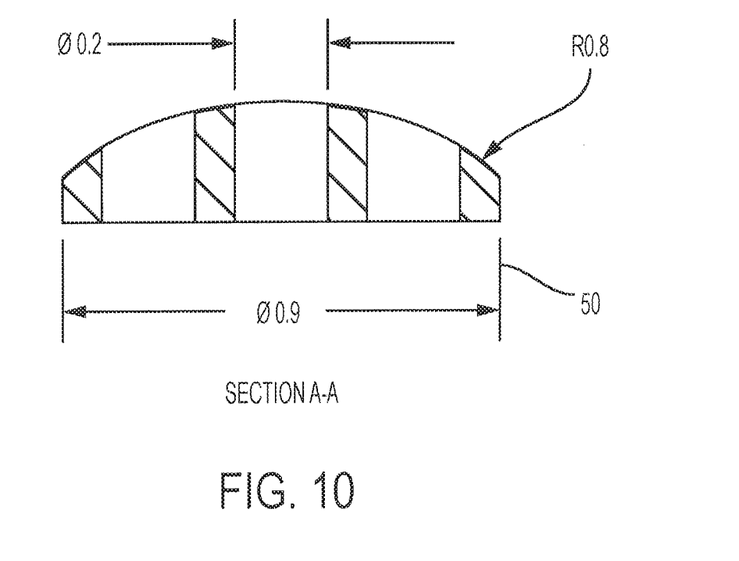
FIG. 10 is a detailed side perspective view of an exemplary embodiment of a disk element of the end effector as shown in FIG. 7.
Figure 11:
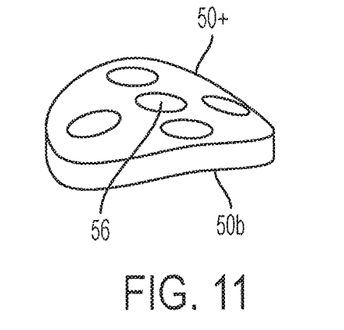
FIG. 11 is a detailed overhead perspective view of an exemplary embodiment of a disk element of the end effector as shown in FIG. 7.
Figure 12:
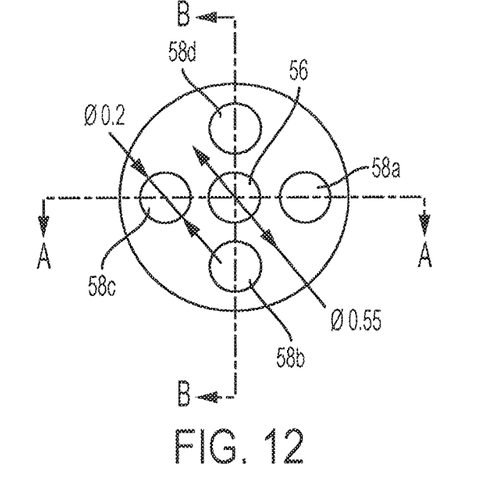
FIG. 12 is a perspective top view of an exemplary embodiment of a disk element of the end effector as shown in FIG. 7.
Figure 13:
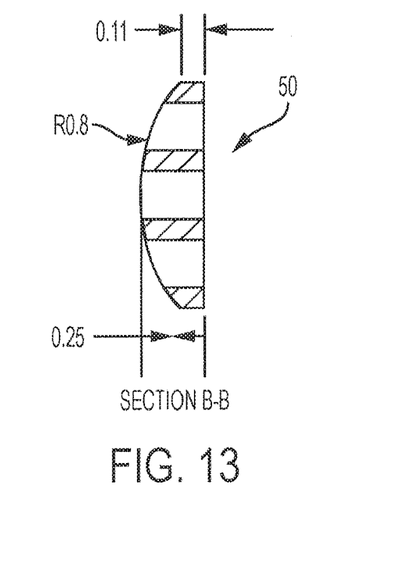
FIG. 13 is a cross-sectional perspective view of an exemplary embodiment of a disk element of the end effector as shown in FIG. 7.

As shown in FIGS. 7-13 an end effector 50 of an ophthalmologic a1 device is shown from the side and front perspectives respectively in the neutral position. The device adapts the principle of the variable neutral-line mechanism. The components include disc-like elements 52, as shown in FIGS. 7 and 8. For example, the elements 50 may be stacked to create the device's distal end 50d. The cable system 32 may be used to actuate the structure 50, but also to maintain the parts 52 together. Instead of flat, the top and bottom surfaces of each element are curved, i.e., cylindrical surfaces as shown in FIGS. 10-13. The axis of the top cylindrical surface 50t is orthogonal to that of the bottom cylindrical surface 50*b*. By assembling the elements alternately in orthogonal directions, the contact surfaces between the adjacent elements form rolling joints 54, as shown in FIG. 7. In other words, at any time, two parts will have one contact line thereby achieving movement. The joint will have two degrees of freedom; the two curved surfaces of each element are offset by 90 degrees. As shown in FIGS. 11 and 12, the center aperture 56 be used to carry a micropipette, or to pass a wire for the micro forceps actuation. The other four apertures 58*a*, 58*b*, 58*c* and 58*d* around the center apertures 56 are used for the actuation wires 32 of the snake-like mechanism. FIG. 9 illustrates the end effector 50 in a 45 bending position. Each disc-like element may be approximately 0.9 mm in diameter, and approximately 0.25 mm in height. All the apertures may be approximately 0.2 mm in diameter. The radius of the cylindrical surfaces is 0.8 mm. Nitinol wires with a diameter of 0.125 mm are used for actuation.

Figure 14:
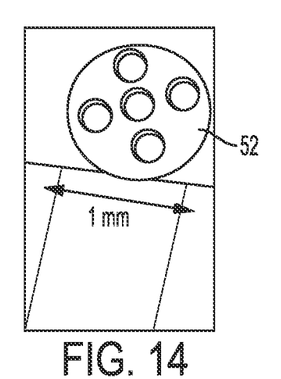
FIG. 14 is an over perspective view of an exemplary embodiment of a disk element of the end effector as shown in FIG. 7.
Figure 15:
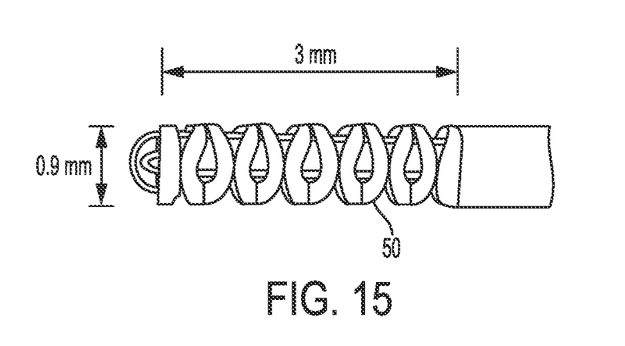
FIG. 15 is a side perspective view of an exemplary embodiment of an end effector as shown of the ophthalmological surgical system.
Figure 16:
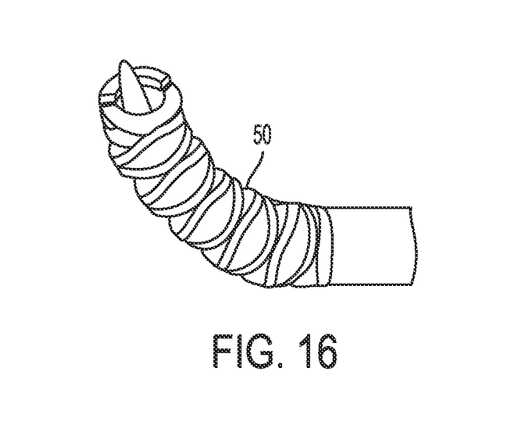
FIG. 16 is a side perspective view of an exemplary embodiment of an end effector as shown of the ophthalmological surgical system articulated about a 90 degree angle.

As shown in FIG. 14, the disc-like elements 50 may be fabricated of a variety of materials including for example brass and suitably micro-machined. In FIG. 15, the end effector 50 is shown from a side perspective view in a neutral position. The proximal end of the device is shown attached to the cylindrical tube. In FIG. 16 the end effector 50 is shown from a side perspective view in a bending position close to 90 degrees.

Referring back to FIGS. 7 and 8, pretension in the actuation wires can maintain the disc-like elements positioned together. Preferably, an optimal pretension level to apply on the device is determined. For instance, hertz theory can be employed to determine a maximum pretension. Thus, for example, first the rolling joint can be considered as the contact of two identical cylinder with the radius r=0:8 mm. The forces exerted by the four wires are modeled as an equivalent force applied in the center, normal to the contact surface. The contact region is a rectangle with a length l=0.9 mm, and a width of 2b, where b is defined as follows:

$$b = \sqrt{\frac{4Fr}{\pi l E}}$$

Where b and 1 denote the half width and the length of the rectangular contact region, respectively, r denotes the radius of the cylinders, and E denotes the Young's modulus of brass. The maximal pressure between the cylinders Pmax can be calculated:

$$P_{max} = \frac{2F_{max}}{\pi b l}$$

The maximal pressure should not exceed the material yield stress, =97 MPa for brass. F can be calculated by setting Pmax=and plugging (1) into (2):

$$F_{max} = \frac{\pi r l \sigma^2}{E}$$

Figure 18:
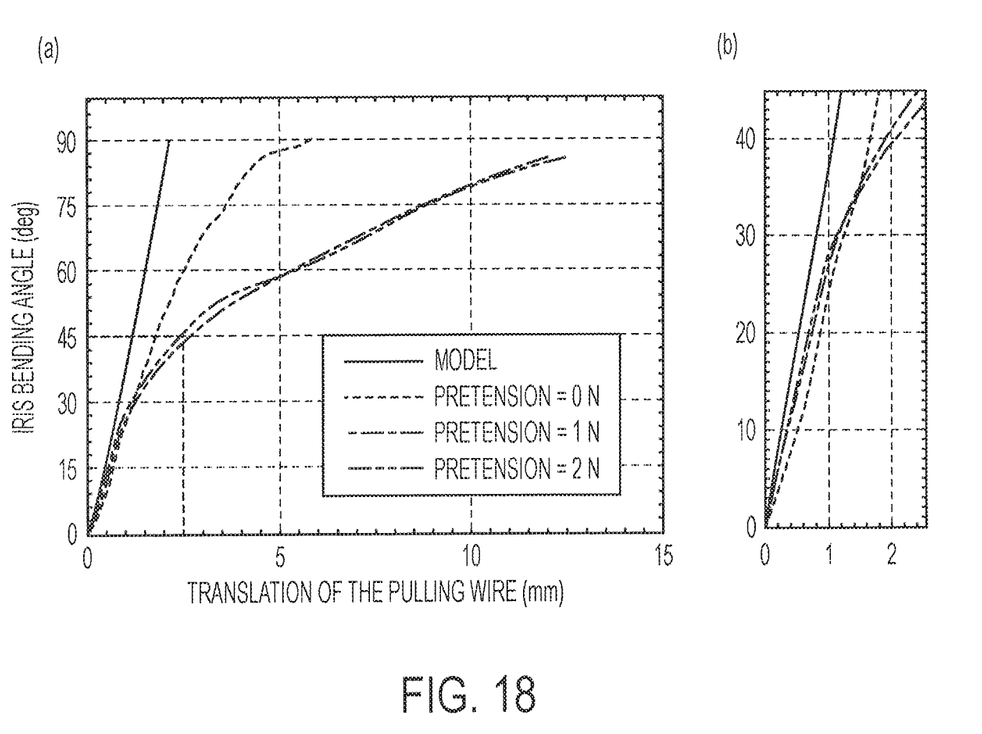
FIGS. 18A-18B is a graph illustrating experimental results, including an exemplary theoretical results derived from kinematic models.

Substituting the variables in, the maximal pretension is determined as 0.8 N. If the pretension is equally distributed among the four wires, each wire should be pre-tensioned less than 0.2 N As shown in FIG. 18 the mathematical relationship between the bending angle of the manipulator and the displacement is depicted. For initial evaluation, a 5:1 scale-up model of the IRIS distal dexterous or the device unit is built using rapid prototyping. The disc-like elements are 3D-printed with an Objet PolyJet printer. The material used is VeroWhite. Instead of nitinol wires, fishing lines are used for actuation. The scale-up model may be mounted on the experimental setup.

The experiment is to determine the relationship between the bending angle of the scale-up IRIS with respect to the wire translation under different pretensions, i.e., 0 N, 1 N, and 2 N. Compression springs are used to apply pretension to the scale up IRIS. A micrometer positioning stage, labeled as linear stage 1 can be used to adjust the pretension. Only one fishing line is used as the actuation wire, while the other three are tensioned with the compression springs. The actuation wire is connected to a second micrometer positioning stage (linear stage 2) through a force sensor. The user can manually control the travel of the actuation wire with linear stage 2. The actuation force can be measured by the force sensor. The bending angle is read directly using a protractor.

FIG. 18 shows the experimental results, together with the theoretical results derived from the kinematics model. When the bending angle is small, e.g., less than 30, the theoretical and experimental results can be relatively consistent. As the pretension increases, more linear translation of the actuation wire is required to achieve the same bending angle. The greater the bending angle is, the longer the extra wire travel needs to be applied. This is likely due to the increased friction and the elastic deformation of the fishing lines. The preliminary experimental results demonstrate that the scale-up device can provide the ability to reach large bending angles, and the kinematics model can predict the required wire translation when the friction is not significant. Empirical model is potentially more useful to provide the more accurate kinematics for large range of motion.

Figure 17:
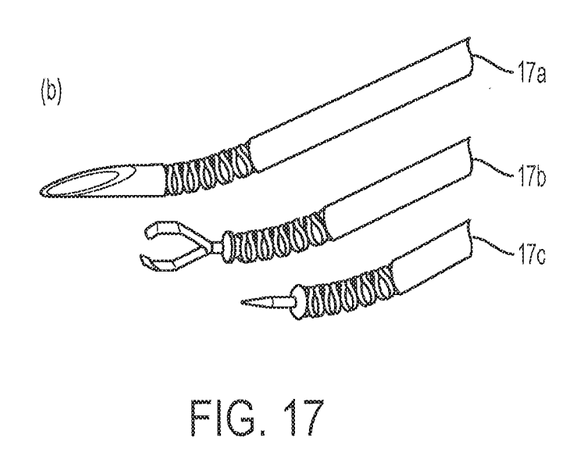
FIGS. 17A-17C are side perspective views of an exemplary embodiment of a plurality of distal tips configurable to the end effector as shown in FIG. 15.

The device and methods described herein have a number of advantages over existing techniques for intraocular dexterity into the ophthalmic tools such as, for example, enhanced surgical capabilities. Advantageously, the benefits of high dexterity with a very small form factor, it can also be applied to other interventional procedures, for example, neuro-endoscopy, sinus surgery, intra-cardiac surgery, and biopsy. As shown in FIGS. 17A-17C several exemplary embodiments of the potential device applications are depicted. For instance, the device can be integrated into the tip of a catheter, enhancing its motion capability. The device can also be incorporated as a needle tip, transforming the regular needle to an actively steerable needle. There is potentially a broad range of applications that can take advantage of this technology. As a result of this device, surgeons may have improved dexterity within the patient's eye to enable more flexible, more advanced surgical procedures.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A dexterous manipulation device comprising:
an end effector that:
1) has a cross-section of from 0.4 mm to 1 mm;

2) can articulate in a working space less than 4 mm by 4 mm;
3) has greater than 90-degrees of rotation with two degrees of freedom; and
4) includes disc elements each having concave top and bottom surfaces,
wherein the disc elements are stacked alternating in orthogonal directions with the concave top and bottom surfaces of adjacent disc elements forming a rolling joint,
wherein each disc element is a solid disc having a plurality of apertures formed therethrough, and
wherein the plurality of apertures includes a center aperture and a plurality of surrounding apertures, each of the plurality of apertures having a substantially similar diameter.

2. The device of claim 1 wherein the device is robotically controlled.

3. The device of claim 1 wherein the device is manually controlled.

4. The device of claim 1 wherein the end effector is less than 0.9 mm in diameter.

5. The device of claim 1 wherein the end effector is less than 3 mm in length.

6. The device of claim 1 wherein the end effector has a cross-section of 0.5 mm or greater.

7. The device of claim 1 wherein the end effector has a cross-section of 0.6 mm or greater.

8. The device of claim 1 further comprising an actuation unit.

9. The device of claim 8 wherein the actuation unit comprises a housing, a motion scaling system, a motor disposed within the actuation unit and the actuation unit comprises a plurality of pulleys.

10. The device of claim 1 further comprising a body unit mated with an actuation unit.

11. The device of claim 10 wherein a plurality of actuation wires extends along the body unit.

12. The device of claim 1 wherein the end effector comprises a needle tip.

13. The device of claim 1 wherein the end effector comprises forceps.

14. The device of claim 1 wherein the end effector comprises a pipette.

15. The device of claim 1 wherein the device is an intra-ocular device.

16. A method for treating a subject comprising:
contacting tissue of the subject with the device of claim 1.

17. A surgical system comprising an actuation unit; a cylindrical body unit; and an end effector that 1) has a cross-section of 0.4 to 1 mm; 2) can articulate in a working space less than 4 mm by 4 mm; and 3) has greater than 90-degrees of rotation with two degrees of freedom, wherein the end effector further comprises a plurality of connected disc elements to provide at least two degrees of rotational freedom, wherein the disc elements are stacked and assembled alternating in orthogonal directions and concave top and bottom surfaces of adjacent disc elements form a rolling joint, wherein each disc element is a solid disc having a plurality of apertures formed therethrough, and wherein the plurality of apertures includes a center aperture and a plurality of surrounding apertures, each of the plurality of apertures having a substantially similar diameter.

18. The surgical system of claim 17 wherein the actuation unit comprises 1) one or more motors and 2) a motor scaling transmission.

19. The surgical system of claim 17 wherein the body unit comprises a cabling system having a plurality of actuation wires to connect with a motor scaling transmission.

20. A device, comprising:
an actuation unit that includes a proximal portion and a distal portion;
a cylindrical body that includes a proximal end and a distal end; and
an end effector having a proximal end and a distal end,
wherein the proximal end of the cylindrical body is configured to connect to the distal portion of the actuation unit and the distal end of the cylindrical body is configured to be coupled to the proximal end of the end effector, wherein the end effector is configured to articulate about an axis in a working space less than 3 mm by 3 mm,
wherein the end effector includes disc elements each having concave top and bottom surfaces, wherein the disc elements are stacked alternating in orthogonal directions with the concave top and bottom surfaces of adjacent disc elements forming a rolling joint,
wherein each disc element is a solid disc having a plurality of apertures formed therethrough, and
wherein the plurality of apertures includes a center aperture and a plurality of surrounding apertures, each of the plurality of apertures having a substantially similar diameter.

21. The device of claim 20, wherein the size of the end effector is less than 0.9 mm in diameter.

22. A surgical system comprising:
an actuation unit that includes a proximal portion and a distal portion having a housing;
an elongated cylindrical body having a hollow inner lumen that extends from a proximal end and a distal end of the elongated cylindrical body; and
an end effector having a proximal end and a distal end wherein the distal end has a diameter of less than 1 mm and a length of less than 3 mm configured to articulate in a working space less than 3 mm by 3 mm,
wherein the proximal end of the cylindrical body is configured to connect to the distal portion of the actuation unit and the distal end of the cylindrical body is configured to be coupled to the proximal end of the end effector,
wherein the end effector includes disc elements each having concave top and bottom surfaces, wherein the disc elements are stacked alternating in orthogonal directions with the concave top and bottom surfaces of adjacent disc elements forming a rolling joint,
wherein each disc element is a solid disc having a plurality of apertures formed therethrough, and
wherein the plurality of apertures includes a center aperture and a plurality of surrounding apertures, each of the plurality of apertures having a substantially similar diameter.

23. The surgical system of claim 22, wherein the actuation unit having a housing includes,
a plurality of motors disposed within the housing;
a motor scaling transmission disposed within the housing configured to individually control a lever mechanism; and
a plurality of pulley guides configured to route a cabling system within the housing.

* * * * *